United States Patent
Su (10) Patent No.: US 9,205,380 B2
(45) Date of Patent: Dec. 8, 2015

(54) MEMBRANE TECHNOLOGY FOR USE IN A METHANOL-TO-PROPYLENE CONVERSION PROCESS

(71) Applicant: Paul Su, Saratoga, CA (US)

(72) Inventor: Paul Su, Saratoga, CA (US)

(73) Assignee: Membrane Technology and Research, Inc., Newark, CA (US)

( * ) Notice: Subject to any disclaimer, the term of this patent is extended or adjusted under 35 U.S.C. 154(b) by 159 days.

(21) Appl. No.: 13/776,362

(22) Filed: Feb. 25, 2013

(65) Prior Publication Data

US 2013/0303819 A1 Nov. 14, 2013

Related U.S. Application Data

(60) Provisional application No. 61/644,121, filed on May 8, 2012.

(51) Int. Cl.
| | |
|---|---|
| *C07C 1/22* | (2006.01) |
| *B01D 61/36* | (2006.01) |
| *B01D 53/22* | (2006.01) |
| *C07C 1/20* | (2006.01) |
| *C07C 7/144* | (2006.01) |

(52) U.S. Cl.
CPC ............ *B01D 61/36* (2013.01); *B01D 53/22* (2013.01); *C07C 1/20* (2013.01); *C07C 1/22* (2013.01); *C07C 7/144* (2013.01)

(58) Field of Classification Search
CPC .............. C07C 7/00; C07C 7/11; C07C 7/12; C07C 7/144
USPC ................................ 585/638, 639, 640, 641
See application file for complete search history.

(56) References Cited

U.S. PATENT DOCUMENTS

| | | | | |
|---|---|---|---|---|
| 6,444,869 | B2 * | 9/2002 | Senetar et al. | 585/809 |
| 6,544,316 | B2 * | 4/2003 | Baker et al. | 95/55 |
| 7,626,067 | B2 * | 12/2009 | Van Egmond et al. | 585/640 |
| 2009/0187056 | A1 * | 7/2009 | Chewter et al. | 585/638 |

* cited by examiner

*Primary Examiner* — In Suk Bullock
*Assistant Examiner* — Sharon Pregler
(74) *Attorney, Agent, or Firm* — Timothy A. Hott; Janet Farrant (57) ABSTRACT

Disclosed herein is a methanol-to-propylene (MTP) conversion process that utilizes a membrane separation step to increase the recycle of $C_2$ hydrocarbons back to the MTP reactor, thereby increasing propylene product yield and reducing raw material loss.

21 Claims, 6 Drawing Sheets

FIG. 1A
(not in accordance with invention)

FIG. 1B
(not in accordance with invention)

MEMBRANE TECHNOLOGY FOR USE IN A METHANOL-TO-PROPYLENE CONVERSION PROCESS

FIELD OF THE INVENTION

The invention relates to a methanol-to-propylene (MTP) conversion process that utilizes a membrane-based gas separation step to enhance propylene product yield.

BACKGROUND OF THE INVENTION

Propylene is the second most important feedstock in the petrochemical industry, after ethylene. It is the raw material for a wide variety of products, including polypropylene, which accounts for nearly two-thirds of all demand. In 2008, worldwide sales of propylene reached a value of over 90 billion U.S. dollars, and demand continues to increase.

There are two traditional routes to propylene production: steam cracking, whereby naphtha or other hydrocarbons are reacted with steam to make light olefins; and fluid catalytic cracking (FCC), which is the refinery operation that breaks down larger hydrocarbons to produce naphtha-weight components for gasoline, as well as olefins and heating oils.

Propane dehydrogenation (PDH) can also be used to produce propylene. Metathesis of ethylene and butane is yet another route to propylene production.

There are currently two commercial processes to produce propylene from methanol: the methanol-to-olefin (MTO) process, which produces roughly 50% ethylene and 50% propylene, and the methanol-to-propylene (MTP) process, which produces 100% propylene. PDH and MTO/MTP are "on demand" processes that are cost-effective when oil prices are high and prices of other alternative energy sources such as coal or natural gas are low.

Methanol-to-propylene (MTP) conversion is an emerging technology that is starting to be commercialized in some areas of the world where feedstocks for conventional processes are in short supply. In the MTP process, methanol is dehydrated to produce dimethyl ether, which is then converted to propylene, with byproducts such as $C_2$, $C_4$, $C_5$, and $C_6$ olefins, aromatics, and paraffins. After passing through a downstream separation train that usually includes multiple distillation columns, many of these byproducts are recycled to the main MTP reactor to increase propylene production. For example, the condensed overhead from the de-ethanizer column, which typically contains 90 wt % $C_2$, is sent back to the reactor.

The non-condensed portion of the de-ethanizer overhead contains inerts such as hydrogen and CO that must be purged from the process. However, the overhead stream also contains valuable $C_1$ and $C_2$ hydrocarbons, which are lost from the process in the purge stream, which is typically used as fuel.

Figure 1A:
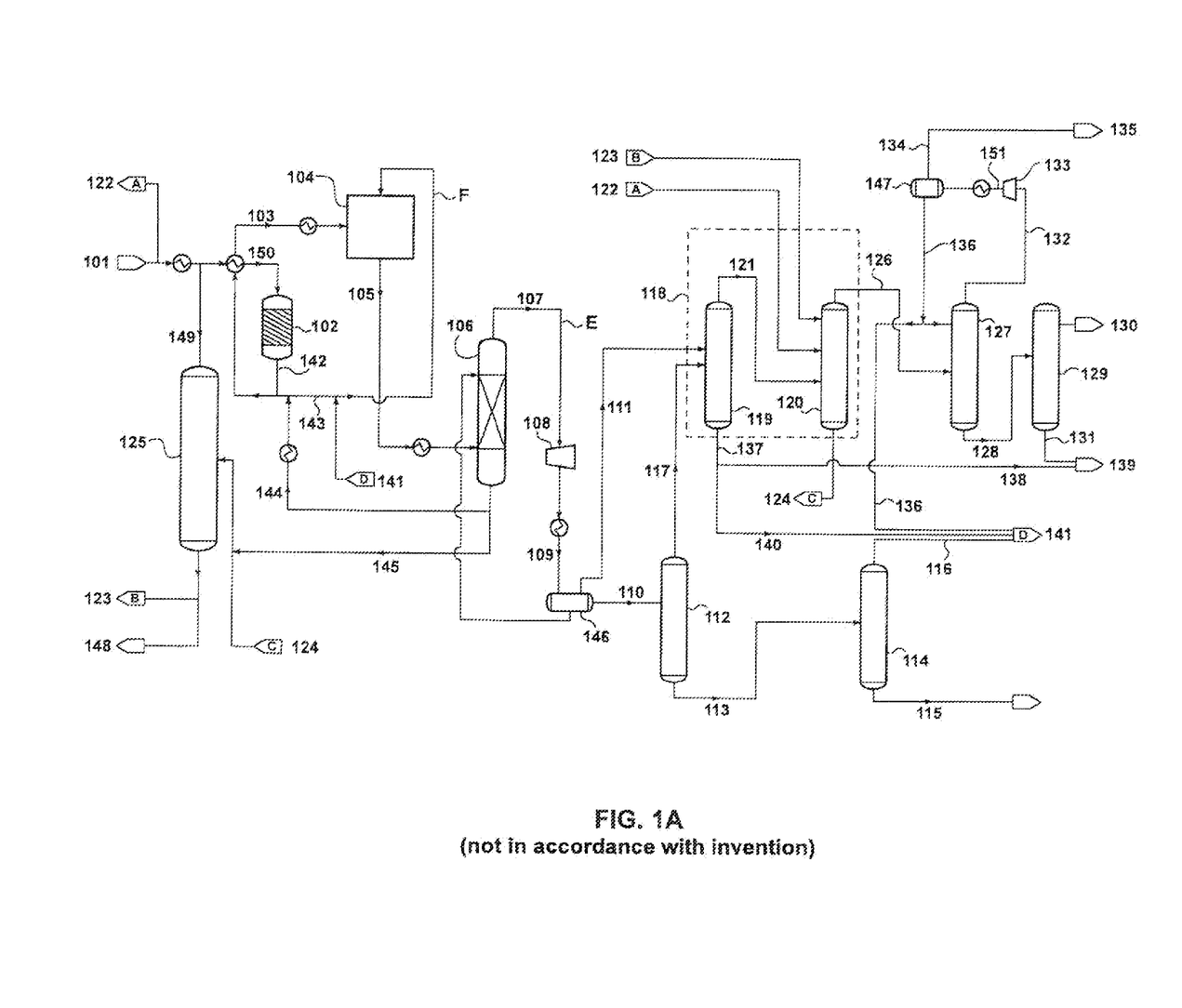
FIG. 1A is a detailed schematic for a standard MTP conversion process (not in accordance with the invention).

FIG. 1A is a detailed schematic for a standard MTP conversion process. The process shown in FIG. 1A involves ten principal pieces of equipment (along with various compressors, heat exchangers, separators, etc.), as follows (from left to right on the figure):

Methanol recovery column, 125;
Dimethyl ether (DME) reactor, 102;
Methanol-to-propylene (MTP) reactor, 104;
Quench column, 106;
Debutanizer column, 112;
DME removal system first column, 119;
DME removal system second column, 120;
Dehexanizer column, 114;
De-ethanizer column, 127; and
Propane-propylene splitter column, 129.

According to the figure, fresh methanol, 101, from an outside source is routed as part of feed stream, 150, to DME reactor, 102. DME stream, 142, emanating from DME reactor 102, is then split into two streams: Stream, 103, which passes through heat exchange steps to MTP reactor, 104, to better control the reactor temperature; and stream, 143, which mixes with other recycle streams and is then sent to the reactor 104.

Resulting stream, 105, from MTP reactor 104 is passed to quench column, 106. Resulting stream, 107, from quench column 106 is compressed in compressor, 108. The resulting compressed stream, 109, is separated in separator, 146, into a liquid stream, 110, containing mostly $C_3$-$C_5$ hydrocarbons, and a vapor stream, 111, containing mostly, $C_1$-$C_4$ hydrocarbons.

Heavier hydrocarbon-containing liquid stream 110 is sent to debutanizer, 112, and separated into a liquid stream, 113, containing mostly $C_4$-$C_5$ and heavier hydrocarbons, and a vapor stream, 117, containing mostly $C_3$-$C_4$ and lighter hydrocarbons.

Heavier hydrocarbon-containing liquid stream 113 is sent to dehexanizer column, 114, and separated into a liquid stream, 115, containing mostly $C_{5+}$ hydrocarbons, and a vapor stream, 116, containing mostly $C_4$-$C_5$ hydrocarbons. Liquid stream 115 can be sent for use in gasoline.

Lower hydrocarbon-containing stream 111 and stream 117 from debutanizer 112 are sent for treatment in DME removal system 118, which includes two columns, 119 and 120. Streams 111 and 117 enter first column 119. Stream, 121, containing mostly $C_1$-$C_3$ hydrocarbons, is withdrawn from first column 119 and sent to second column, 120, where it is contacted with methanol, 122, and water, 123. Liquid stream, 124, containing mostly methanol, DME, and water, is withdrawn from the bottom of second column 120. Stream 124 is sent back to the process at position C on the schematic, where it enters the methanol recovery column, 125.

Vapor stream, 126, containing mostly $C_1$-$C_3$ hydrocarbons, is withdrawn from the top of second column 120 and sent to de-ethanizer 127. Liquid stream, 128, containing mostly $C_3$ hydrocarbons, is sent to propane-propylene splitter column, 129. Propylene in vapor form is withdrawn from the top of propylene/propane splitter column 129 and then condensed (condenser not shown) to produce liquid propylene product, 130. Liquid propane, 131, is withdrawn from the bottom of column 129.

Returning to de-ethanizer column 127: A vapor stream, 132, containing mostly $C_1$ and $C_2$, as well as some inerts (typically $H_2$ and CO) is withdrawn from the top of column 127, then compressed in compressor, 133. The resulting compressed stream, 151, is routed to separator, 147. The non-condensed portion, 134, of compressed stream 151, containing mostly inerts and some residual $C_1$ and $C_2$ hydrocarbons, is withdrawn as a purge stream, which can be sent for use as fuel gas, 135.

The condensed portion, 136, of compressed stream 151, containing mostly $C_1$ and $C_2$ hydrocarbons, is split into two portions, one of which is recycled to the de-ethanizer column. The other portion of stream 136 joins stream 116 (containing mostly $C_4$-$C_5$ hydrocarbons) and stream 140 (discussed below) and is sent as hydrocarbon recycle stream, 141, back to the process at position D on the schematic. Hydrocarbon recycle stream 141 joins stream 143, which is then routed to MTP reactor 104.

Returning to first DME column 119: A liquid stream, 137, containing mostly $C_4$ hydrocarbons, is withdrawn from the bottom of column 119. A portion, 138, of this stream is sent with propane stream 131 to make liquid petroleum gas (LPG), 139.

The remaining portion, 140, of stream 137 joins streams 116 and 136 and is sent as hydrocarbon recycle stream, 141, back to the process at position D on the schematic. The recycle stream 141 contains mostly $C_2$-$C_5$ hydrocarbons. As discussed above, this stream joins stream 143 and is routed to MTP reactor 104.

Returning to quench column 106: The bottoms stream from this column is split into two streams: Stream, 144, is heat-exchanged and joins streams 141 and 143 to be routed to MTP reactor 104; stream 145 joins stream 124 (both of which contain mostly methanol, DME, and water), to be routed to methanol recovery column 125.

The bottoms stream from methanol recovery column 125—which contains mostly water—is split into two streams: Stream 123, is routed to the second column 120 of DME removal system 118 at position B; stream 148 is purged.

Stream, 149, from the top of methanol recovery column 125, contains mostly methanol and DME, and joins stream 101 to be muted as feed stream 150 to DME reactor 102.

Figure 1B:
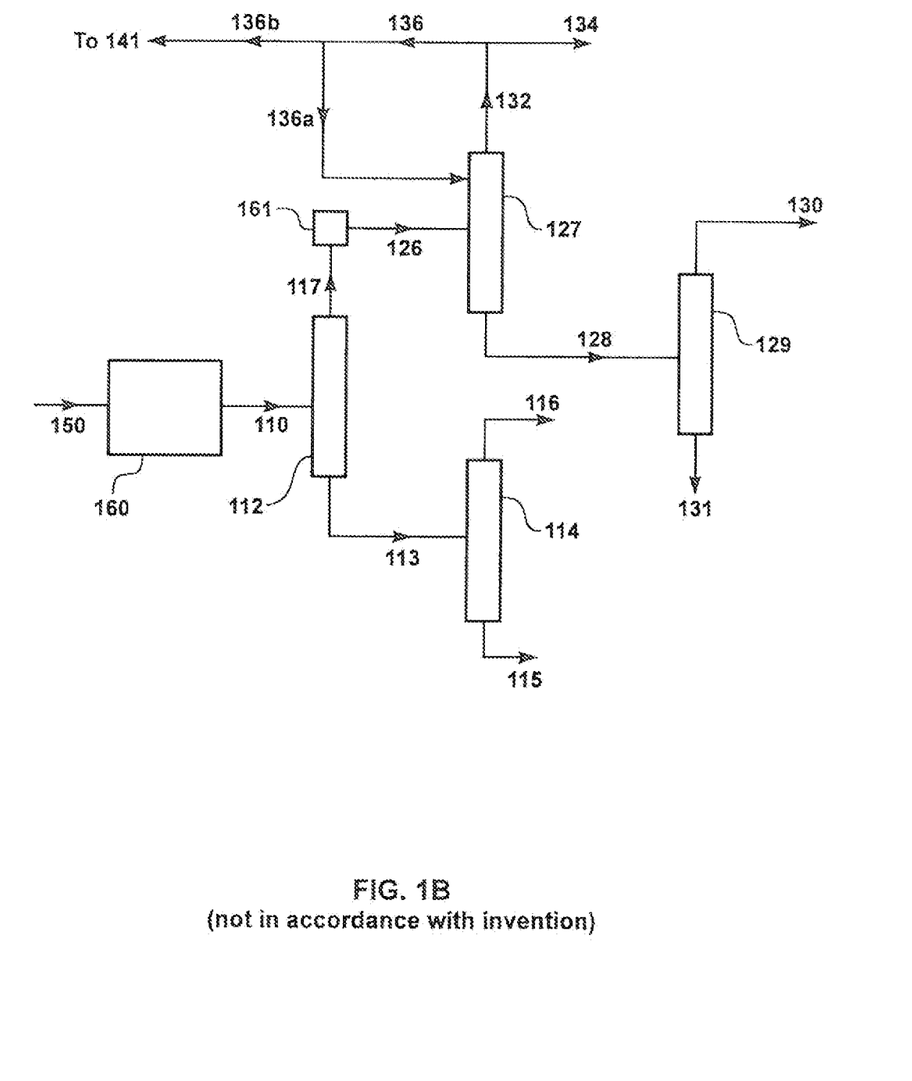
FIG. 1B is a greatly simplified schematic for the MTP conversion process shown in FIG. 1A (not in accordance with the invention).

FIG. 1B is a greatly simplified schematic for the MTP conversion process shown in FIG. 1A. Referring to the figure, feed stream 150 is routed to reactor train, 160. Referring back to FIG. 1A, reactor train 160 consists of dimethyl ether (DME) reactor, 102; MTP reactor, 104; quench column, 106; methanol recovery column, 125; and associated equipment.

Heavier hydrocarbon-containing liquid stream 110 is sent to debutanizer 112 and separated into liquid stream 113, containing mostly $C_4$-$C_5$ and heavier hydrocarbons, and vapor stream 117, containing mostly $C_3$-$C_4$ and lighter hydrocarbons.

Heavier hydrocarbon-containing liquid stream 113 is sent to dehexanizer 114 and separated into liquid stream 115, containing mostly $C_{5+}$ hydrocarbons, and vapor stream 116, containing mostly $C_4$-$C_5$ hydrocarbons. As discussed previously, liquid stream 115 can be sent for use in gasoline.

After passing through the DME removal system, 161 (columns 119 and 120 in FIG. 1), stream 117 is sent as vapor stream 126, containing mostly $C_1$-$C_3$ hydrocarbons, to de-ethanizer 127. Liquid stream 128, containing mostly $C_3$ hydrocarbons, is sent to propylene/propane splitter column 129. Propylene in vapor form is withdrawn from the top of propylene/propane splitter column 129 and condensed (condenser not shown) to produce liquid propylene product 130. Liquid propane 131 is withdrawn from the bottom of column 129.

Vapor stream 132, containing mostly $C_1$ and $C_2$, as well as some inerts, is withdrawn from the top of column 127, then compressed and condensed (compressor and condenser not shown in FIG. 1B). The non-condensed portion, 134, contains mostly inerts and some residual $C_1$ and $C_2$ hydrocarbons and is withdrawn as a purge stream, which can be sent for use as fuel gas, as discussed above.

The condensed portion, 136, containing mostly $C_1$ and $C_2$ hydrocarbons, is split into two portions, 136a and 136b. Portion 136a is recycled to the de-ethanizer column. Referring back to FIG. 1A, portion 136b joins streams 116 and 140 and is sent as hydrocarbon recycle stream 141 back to the process at position D on the schematic. Hydrocarbon recycle stream 141 joins stream 143, which is then routed to MTP reactor 104.

SUMMARY OF THE INVENTION

The invention is a methanol-to-propylene (MTP) conversion process that utilizes a membrane separation step. Depending on the type of membranes used, either the residue stream or the permeate stream may be recycled back to various positions upstream in the process, thereby reducing feedstock losses and increasing propylene product yield.

A basic process of the invention utilizes membranes that are selective to hydrogen over $C_2$ hydrocarbons in the membrane separation step. The membrane is typically also selective for carbon oxides (i.e., carbon monoxide and carbon dioxide) over $C_2$ hydrocarbons.

This process embodiment comprises the following steps:
(a) performing an operation to convert methanol to propylene, said operation including at least one reaction step and at least one propylene recovery step;
(b) withdrawing from the operation a gas stream comprising hydrogen, carbon monoxide, carbon dioxide, and $C_1$ and $C_2$ hydrocarbons;
(c) providing a membrane having a feed side and a permeate side, wherein the membrane is selective to hydrogen over $C_2$ hydrocarbons;
(d) passing the gas stream as a feed stream across the feed side;
(e) withdrawing from the permeate side a permeate stream that is depleted in $C_2$ hydrocarbons relative to the gas stream;
(f) withdrawing from the feed side a residue stream that is enriched in $C_2$ hydrocarbons relative to the gas stream; and
(g) passing the residue stream as a recycle stream back to step (a).

The membrane residue stream may be recirculated at any convenient point within the reaction and separation sub-steps that make up step (a)—typically to a point in the MTP conversion operation where the pressure is at least 1 bar less than the feed stream pressure, to account for pressure drop across the membrane. In one embodiment, the membrane residue stream is recycled back to a compressor located downstream of a de-ethanizer column. Alternatively, the residue stream may be recycled back to a compressor downstream of a quench column, or directly back to a methanol-to-propylene reactor.

In accordance with this embodiment, the membrane preferably comprises a glassy polymer. The membrane preferably has a selectivity for hydrogen over ethylene of at least 10 and, more preferably, at least 15 or 20. The membrane preferably has a hydrogen permeance of at least about 500 gpu and, more preferably, at least about 1,000 gpu.

An alternative process embodiment of the invention utilizes membranes that are selective to $C_2$ hydrocarbons over hydrogen. The membrane is typically also selective for $C_2$ hydrocarbons over carbon oxides.

A basic embodiment of this process comprises the following steps:
(a) performing an operation to convert methanol to propylene, said operation including at least one reaction step and at least one propylene recovery step;
(b) withdrawing from the operation a gas stream comprising hydrogen, carbon monoxide, carbon dioxide, and $C_1$ and $C_2$ hydrocarbons;
(c) providing a membrane having a feed side and a permeate side, wherein the membrane is selective to $C_2$ hydrocarbons over hydrogen;
(d) passing the gas stream across the feed side;
(e) withdrawing from the feed side a residue stream that is depleted in $C_2$ hydrocarbons relative to the gas stream;
(f) withdrawing from the permeate side a permeate stream that is enriched in $C_2$ hydrocarbons relative to the gas stream; and
(g) passing the permeate stream as a recycle stream back to step (a).

The permeate stream may be recycled back to a compressor downstream of a quench column. Alternatively, the permeate stream may be recycled directly back to a methanol-to-propylene reactor, or to any other point in the MTP conversion operation where the pressure is no more than 7 bar gauge (bar g).

In accordance with this embodiment, the membrane preferably comprises a rubbery polymer. The membrane preferably has a selectivity for ethylene over hydrogen of at least 4 and, more preferably, at least 5, 8, or even 0.10. The membrane preferably has a $C_2$ hydrocarbon permeance of at least about 400 gpu and, more preferably, at least about 800 gpu.

A specific embodiment of the invention utilizes two membrane separation steps, where the first membrane separation step utilizes membranes that are selective to hydrogen over $C_2$ hydrocarbons, and the second membrane separation step utilizes membranes that are selective to $C_2$ hydrocarbons over hydrogen. The first membrane is typically also selective for carbon oxides over $C_2$ hydrocarbons, and the second membrane, for $C_2$ hydrocarbons over carbon oxides.

This process embodiment comprises the following basic steps:

(a) performing an operation to convert methanol to propylene, said operation including at least one reaction step and at least one propylene recovery step;

(b) withdrawing from the operation a gas stream comprising hydrogen, carbon monoxide, carbon dioxide, and $C_1$ and $C_2$ hydrocarbons;

(c) providing a first membrane having a first feed side and a first permeate side, wherein the first membrane is selective to hydrogen over $C_2$ hydrocarbons;

(d) passing the gas stream across the first feed side;

(e) withdrawing from the first permeate side a first permeate stream that is depleted in $C_2$ hydrocarbons relative to the gas stream;

(f) withdrawing from the first feed side a first residue stream that is enriched in $C_2$ hydrocarbons relative to the gas stream;

(g) providing a second membrane having a second feed side and a second permeate side, wherein the second membrane is selective to $C_2$ hydrocarbons over hydrogen;

(h) passing the first residue stream across the second feed side;

(i) withdrawing from the second feed side a second residue stream that is depleted in $C_2$ hydrocarbons relative to the first residue stream;

(j) withdrawing from the second permeate side a second permeate stream that is enriched in $C_2$ hydrocarbons relative to the first residue stream; and (k) passing the second permeate stream as a recycle stream back to step (a).

The second permeate stream may be recycled back to a compressor downstream of a quench column. Alternatively, the second permeate stream may be recycled directly to a methanol-to-propylene reactor, or to any other point in the MTP conversion operation, preferably where the pressure is no more than about 7 bar g.

In accordance with this process embodiment, the first membrane preferably comprises a glassy polymer. The first membrane preferably has a selectivity for hydrogen over ethylene of at least 10 and, more preferably, at least 15 or 20. The first membrane preferably has a hydrogen permeance of at least about 500 gpu and, more preferably, at least about 1,000 gpu.

The second membrane preferably comprises a rubbery polymer. The second membrane preferably has a selectivity for ethylene over hydrogen of at least 4 and, more preferably, at least 5, 8, or even 10. The second membrane preferably has a $C_2$ hydrocarbon permeance of at least about 400 gpu and, more preferably, at least about 800 gpu.

The process of the invention results in increased recycle of $C_2$ hydrocarbons to the MTP reactor, thereby increasing product yield and reducing raw material loss.

DETAILED DESCRIPTION OF THE INVENTION

The invention is a methanol-to-propylene (MTP) conversion process that utilizes a membrane separation step to increase the recycle of $C_2$ hydrocarbons back to the MTP reactor, thereby increasing propylene product yield and reducing raw material loss.

Figure 2A:
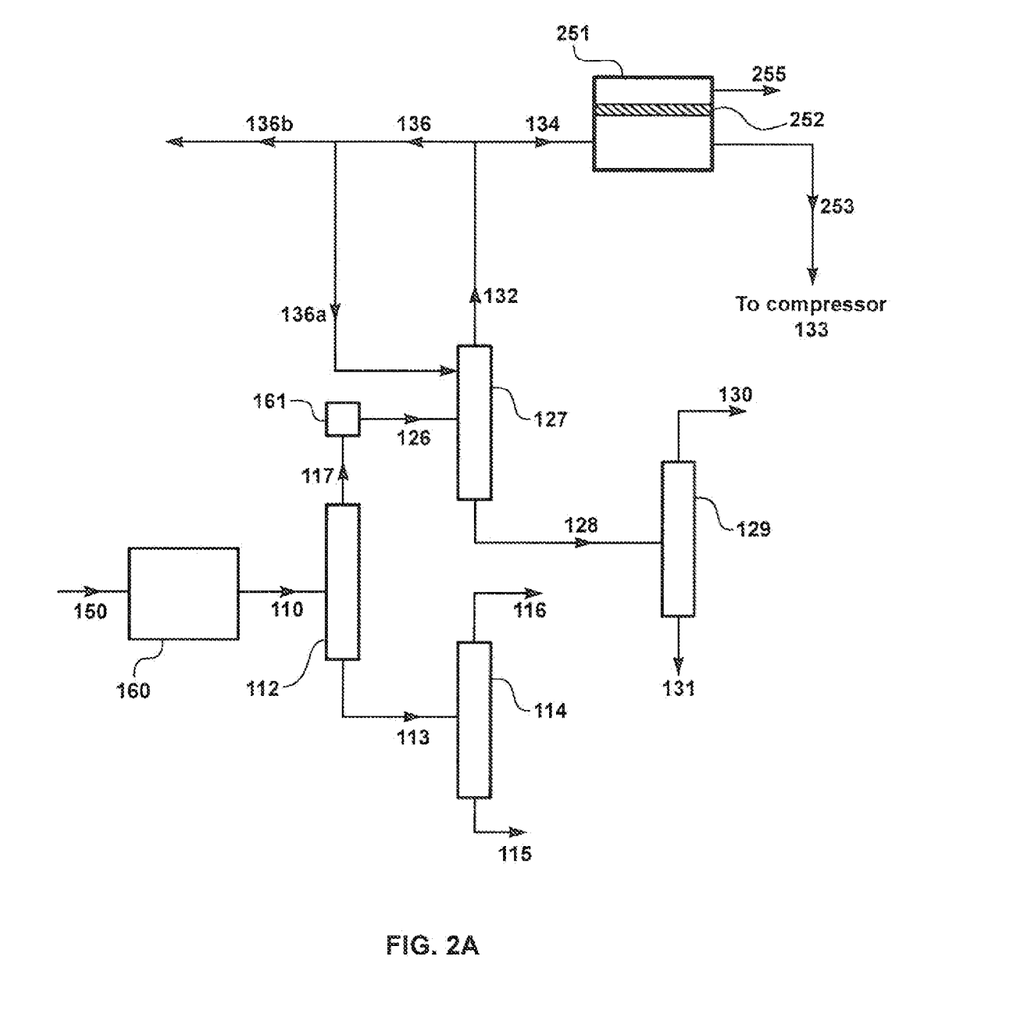
FIG. 2A is a basic process schematic for an MTP conversion process in accordance with the invention, where a stream containing mostly inerts and $C_1$ and $C_2$ hydrocarbons is withdrawn from the top of the de-ethanizer column and processed in a membrane separation unit containing membranes that are selective to hydrogen over $C_1$ and $C_2$ hydrocarbons.
Figure 2B:
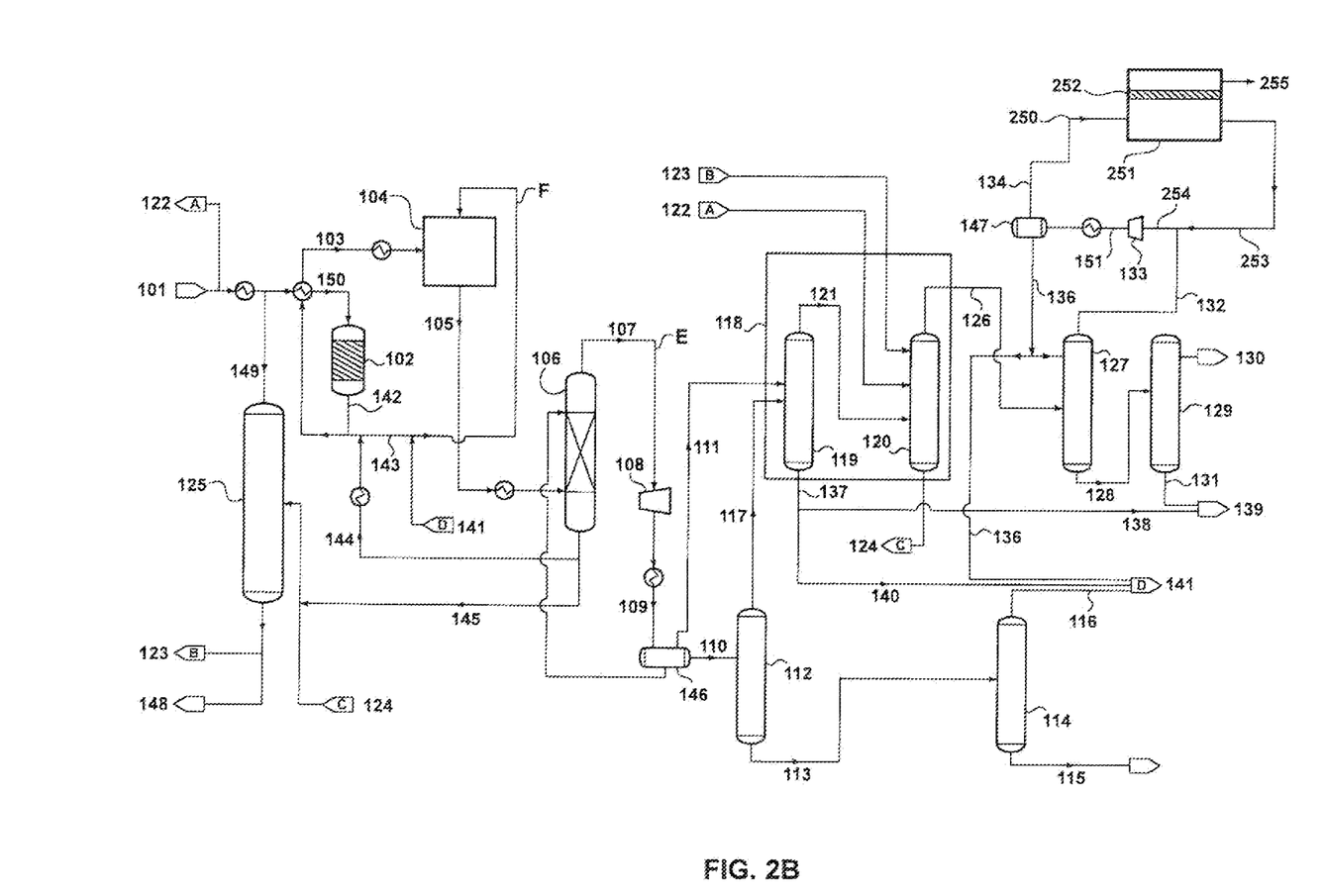
FIG. 2B is a detailed schematic for the MTP conversion process shown in FIG. 2A.

A basic process schematic for an MTP conversion process in accordance with the invention is shown in FIG. 2A; a detailed schematic is shown in FIG. 2B (reference numerals on FIG. 2B correspond to reference numerals on FIG. 1A). The basic process is the same as that shown in FIGS. 1A and 1B, except that stream 134, originating from de-ethanizer column 127, is processed in a membrane separation unit, 251, containing membranes, 252, that are selective to hydrogen over $C_2$ hydrocarbons.

Membranes for use in the embodiment of the invention shown in FIGS. 2A and 2B (which will be described in the Examples section) may comprise any polymer that will preferentially permeate hydrogen over $C_2$ hydrocarbons. Typically, the membrane is also selective for carbon oxides (i.e., carbon monoxide and carbon dioxide) over $C_2$ hydrocarbons. The membrane preferably has a selectivity for hydrogen over ethylene of at least 10 and, more preferably, at least 15 or 20. The membrane also preferably has a hydrogen permeance of at least about 500 gpu and, more preferably, at least about 1,000 gpu.

Preferred membrane materials are "glassy" polymers, such as, for example and without limitation, polyamides, polyimides, polysulfones, polyvinyl alcohol, polypropylene oxide, cellulose derivatives, polyvinylidene fluoride, and polymers having repeating units of fluorinated dioxoles, fluorinated dioxolanes, and fluorinated cyclically polymerizable alkyl ethers.

Particularly preferred membranes for use in the process of the invention have selective layers made from a hydrophobic fluorinated glassy polymer or copolymer. This polymer determines the membrane selectivity. Commercially available fluorinated polymers/copolymers that are suitable for use in the process of the present invention include Hyflon® AD (Solvay Solexis, Inc., Thorofare, N.J.); Cytop® (Asahi Glass Company, Tokyo, Japan); and Teflon® AF (DuPont, Wilmington, Del.). Uses of such materials are described in U.S. Pat. No. 6,544,316.

The polymer chosen for the selective layer can be used to form films or membranes by any convenient technique known in the art, and may take diverse forms. The membrane may take the form of a homogeneous film, an integral asymmetric membrane, a multilayer composite membrane, a membrane incorporating a gel or liquid layer or particulates, or any other form known in the art.

Because the polymers are glassy and rigid, an unsupported film, tube, or fiber of the polymer is usable as a single-layer membrane. However, single-layer films will normally be too thick to yield acceptable transmembrane flux however, and, in practice, the separation membrane usually comprises a very thin selective layer that forms part of a thicker structure, such as an integral asymmetric membrane or a composite membrane.

The preferred form is a composite membrane. Modern composite membranes typically comprise a highly permeable, but relatively non-selective, support membrane that provides mechanical strength, coated with a thin selective layer of another material that is primarily responsible for the separation properties. Typically, but not necessarily, such a composite membrane is made by solution-casting the support membrane, then solution-coating the selective layer. Preparation techniques for making composite membranes of this type are well known.

The membranes may be manufactured as flat sheets or as fibers and housed in any convenient module form, including spiral-wound modules, plate-and-frame modules, and potted hollow fiber modules. The making of all these types of membranes and modules is well-known in the art. Flat-sheet membranes in spiral-wound modules is the most preferred choice.

Membrane unit 251 may contain a single membrane module or bank of membrane modules or an array of modules. A single-stage membrane separation operation is adequate for many applications. If the permeate stream requires further purification, it may be passed to a second bank of membrane modules for a second processing step. If the residue stream requires further concentration, it may be passed to a second bank of membrane modules for a second-stage treatment. Such multi-stage or multi-step processes, and variants thereof, will be familiar to those of skill in the art, who will appreciate that the membrane separation step may be configured in many possible ways, including single-stage, multi-stage, multi-step, or more complicated arrays of two or more units in serial or cascade arrangements.

Stream 134, which is at high pressure after being compressed in compressor 133 (shown in FIG. 2B), flows as a feed stream 250 across the feed surface of membrane 252. The permeate side of the membrane is maintained at lower pressure to provide a driving force for transmembrane permeation. Hydrogen and carbon monoxide permeate the membrane preferentially, resulting in hydrocarbon-enriched residue stream, 253, and hydrocarbon-depleted permeate stream, 255. Typically, the feed side is maintained at a pressure within the range of about 20 bar g to about 40 bar g. The permeate side is typically maintained at a pressure within the range of about 1 bar g to about 25 bar g; preferably, the permeate side is maintained at a pressure of 7 bar g or less.

As is familiar to those of skill in the art, the separation performance achieved by the membrane depends on such factors as the membrane selectivity, the pressure ratio between feed and permeate sides, and the membrane area. The transmembrane flux depends on the permeability of the membrane material, the pressure difference across the membrane, and the membrane thickness.

Hydrocarbon-depleted permeate stream 255 is withdrawn from the permeate side of the membrane unit 251. Stream 255—the major component of which is now the combined contaminants hydrogen and carbon monoxide—can either be flared or sent for use as fuel gas.

Hydrocarbon-enriched membrane residue stream 253 is withdrawn from the feed side of the membrane unit 251. In the embodiment shown in FIGS. 2A and 2B, membrane residue stream 253 is combined with stream 132 and routed as combined stream 254 back to the process upstream of compressor 133 (shown in FIG. 2B), from where it is passed as compressed stream 151 to condenser 147, and thence to recovery via streams 136 and 141 at position D on FIG. 2B.

Alternatively, residue stream 253 can be routed (without the need for compression) back to the process at one (or both) of two positions:

To position E: After quench column 106 and upstream of main compressor 108.

To position F: Directly back to MTP reactor 104.

As yet another option, membrane residue stream 253 can be routed back to any point in the MTP conversion operation where the pressure is at least 1 bar less than the feed stream pressure, to account for pressure drop across the membrane.

Figure 3:
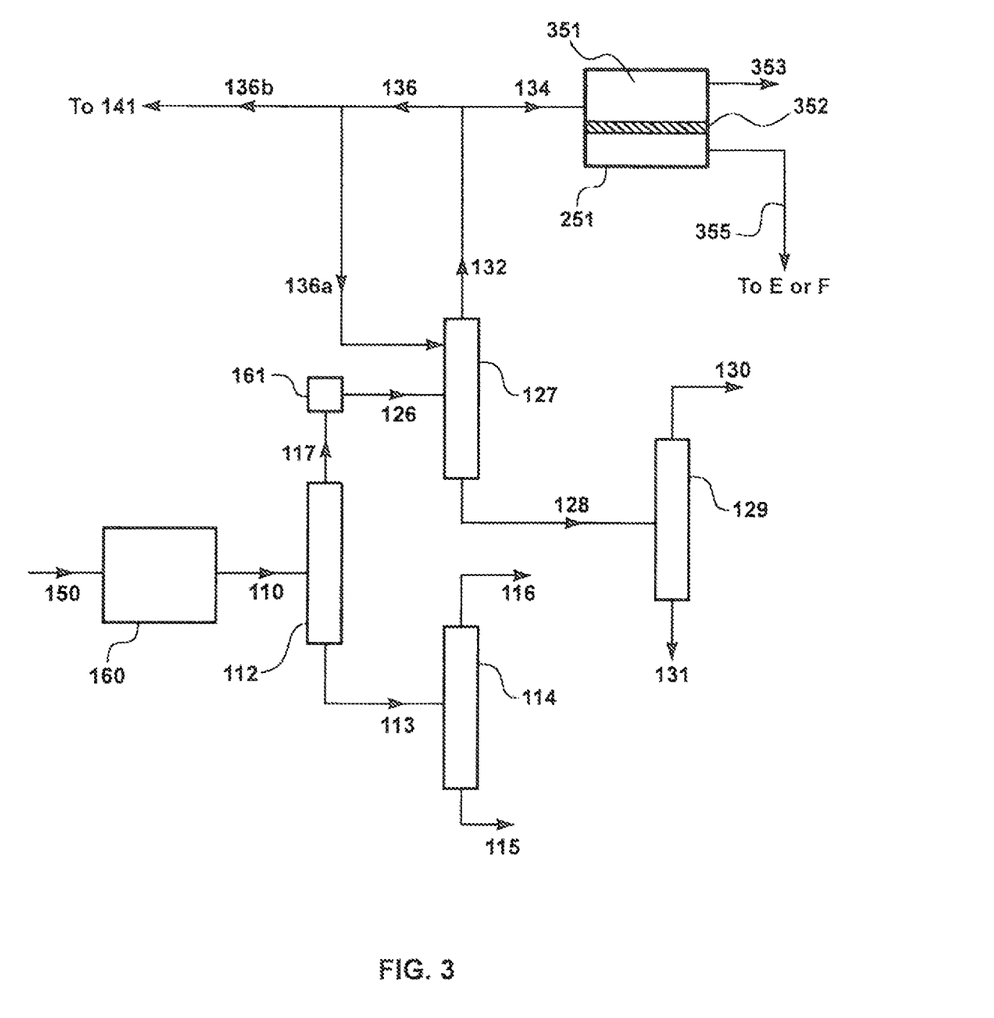
FIG. 3 is a basic process schematic for an MTP conversion process in accordance with an alternative embodiment of the invention, where a stream containing mostly inerts and $C_1$ and $C_2$ hydrocarbons is withdrawn from the top of the de-ethanizer column and processed in a membrane separation unit containing membranes that are selective to $C_1$ and $C_2$ hydrocarbons over hydrogen.

A basic process schematic for an MTP conversion process in accordance with an alternative embodiment of the invention is shown in FIG. 3. The basic process is the same as that shown in FIGS. 1A and 1B, except that stream 134, originating from de-ethanizer column 127, is processed in a membrane separation unit, 351, containing membranes, 352, that are selective to $C_2$ hydrocarbons over hydrogen.

Membranes for use in the embodiment of the invention shown in FIG. 3 may comprise any polymer that will preferentially permeate $C_2$ hydrocarbons over hydrogen. The membrane preferably has a selectivity for ethylene over hydrogen of at least 4 and, more preferably, at least 5, 8, or even 10. The membrane also preferably has a $C_2$ hydrocarbon permeance of at least about 400 gpu and, more preferably, at least about 800 gpu.

In this process embodiment, the membrane 352 is typically made from an elastomeric or "rubbery" polymer. Examples of polymers that can be used to make elastomeric membranes include, but are not limited to, nitrile rubber, neoprene, polydimethylsiloxane (also known as PDMS or silicone rubber), chlorosulfonated polyethylene, polysilicone-carbonate copolymers, fluoroelastomers, plasticized polyvinylchloride, polyurethane, cis-polybutadiene, cis-polyisoprene, poly(butene-1), polystyrene-butadiene copolymers, styrene/butadiene/styrene block copolymers, styrene/ethylene/butylene block copolymers, thermoplastic polyolefin elastomers, and block copolymers of polyethers, polyamides, and polyesters. Membranes where the selective layer comprises PDMS are particularly preferred.

Membrane modules and configurations are as discussed above with respect to the process embodiment shown in FIGS. 2A and 2B.

Feed stream 134, which is at high pressure after being compressed in compressor 133 (shown in FIG. 1A), flows as a feed stream across the feed surface of membrane 352. The permeate side of the membrane is maintained at lower pressure to provide a driving force for transmembrane permeation. $C_1$ and $C_2$ hydrocarbons permeate the membrane preferentially, resulting in hydrocarbon-enriched permeate stream, 355, and hydrocarbon-depleted residue stream, 353. Typically, the feed side is maintained at a pressure within the range of about 20 bar g to about 40 bar g. The permeate side is typically maintained at a pressure within the range of about 1 bar g to about 25 bar g; preferably, the permeate side is maintained at a pressure of 7 bar g or less.

Hydrocarbon-depleted membrane residue stream 353 is withdrawn from the feed side of the membrane unit 351. Stream 353—the major component of which is now the combined contaminants hydrogen and carbon monoxide—can either be flared or sent for use as fuel gas.

Hydrocarbon-enriched permeate stream 355 is withdrawn from the permeate side of the membrane unit 351. Referring to FIG. 1A, permeate stream 355 can then be routed back to the process at one (or both) of two positions:
To position E: After quench column 106 and upstream of main compressor 108.
To position F: Directly back to MTP reactor 104.

As yet another option, permeate stream 355 can be routed back to any point in the MTP conversion operation where the pressure is no more than 7 bar g.

Figure 4:
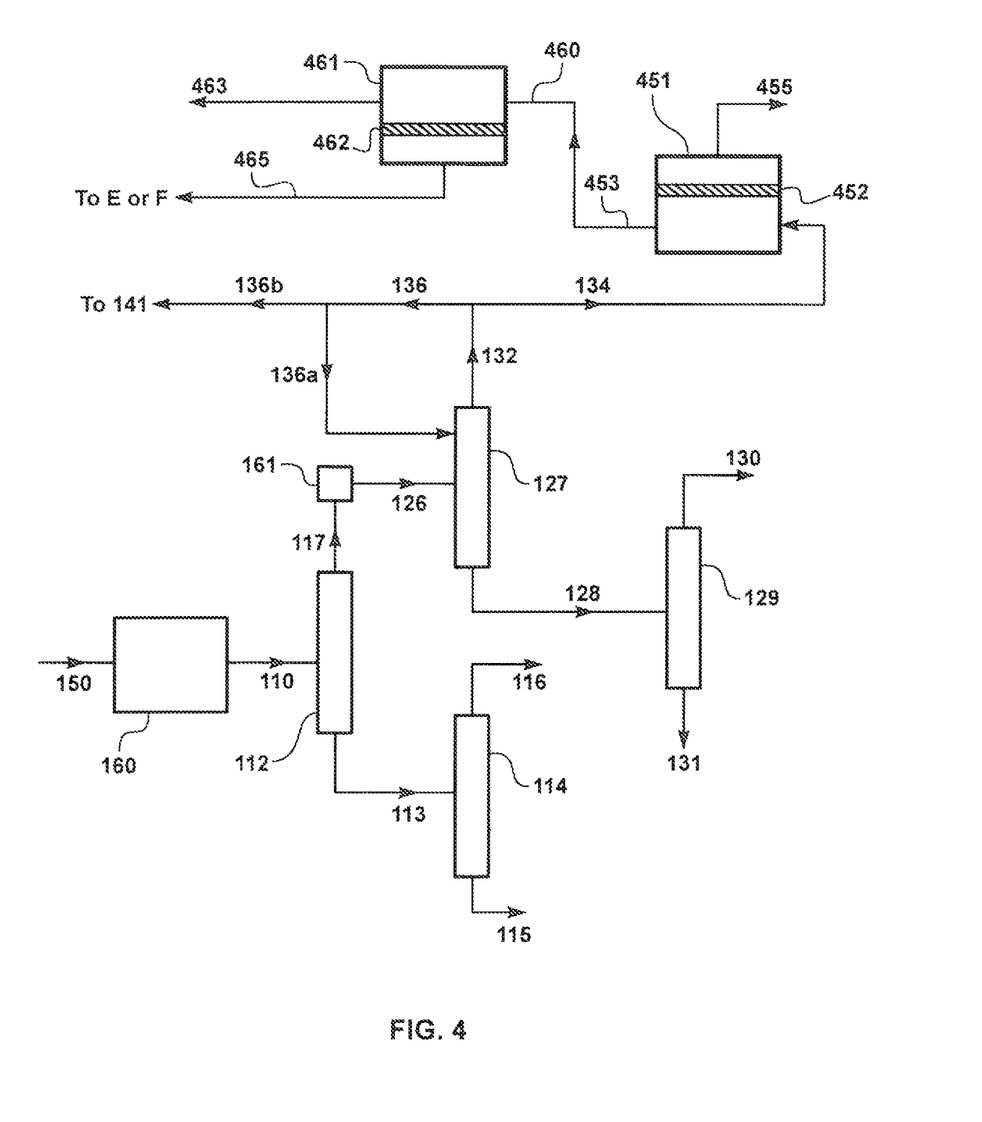
FIG. 4 is process schematic for an MTP conversion process in accordance with a specific embodiment of the invention, where a stream containing mostly inerts and $C_1$ and $C_2$ hydrocarbons is withdrawn from the top of the de-ethanizer column and processed in a first membrane separation unit containing membranes that are selective to hydrogen over $C_1$ and $C_2$ hydrocarbons, followed by processing of the residue stream from the first membrane unit in a second membrane unit containing membranes that are selective to $C_1$ and $C_2$ hydrocarbons over hydrogen.

A process schematic for an MTP conversion process in accordance with a specific embodiment of the invention is shown in FIG. 4. The basic process is the same as that shown in FIGS. 1A and 1B, except that stream 134, originating from de-ethanizer column 127, is processed in a first membrane separation unit, 451, containing membranes, 452, that are selective to hydrogen over $C_2$ hydrocarbons, followed by processing of the residue stream, 453, from the first membrane unit in a second membrane unit, 461, containing membranes, 462, that are selective to $C_2$ hydrocarbons over hydrogen.

Stream 134, which is at high pressure after being compressed in compressor 133 (shown in FIG. 1A), flows as a feed stream across the feed surface of membrane 452. The feed stream is typically heated (heating unit not shown) before being sent to membrane unit 451. The membranes 452 are typically glassy polymeric membranes, as described above with respect to membranes 252 in FIG. 2A. Membrane modules and configurations are also as discussed above with respect to the process embodiment shown in FIGS. 2A and 2B.

As discussed above, the permeate side of the membrane is maintained at lower pressure to provide a driving force for transmembrane permeation. Hydrogen and carbon monoxide permeate the membrane preferentially, resulting in hydrocarbon-enriched residue stream, 453, and hydrocarbon-depleted permeate stream, 455. Typically, the feed side is maintained at a pressure within the range of about 20 bar g to about 40 bar g. The permeate side is typically maintained at a pressure within the range of about 1 bar g to about 25 bar g; preferably, the permeate side is maintained at a pressure of 7 bar g or less.

Hydrocarbon-depleted permeate stream 455 is withdrawn from the permeate side of first membrane unit 451. Stream 455—the major component of which is now the combined contaminants hydrogen and carbon monoxide—can either be flared or sent for use as fuel gas.

Hydrocarbon-depleted membrane residue stream 453 is withdrawn from the feed side of the membrane unit 451, and is routed as a feed stream to second membrane unit 461 containing membranes 462 that are selective to $C_1$ and $C_2$ hydrocarbons over hydrogen. Membranes 462 are typically rubbery polymeric membranes, as described above with respect to membranes 352 in FIG. 3. Membrane modules and configurations are again as discussed above with respect to the process embodiment shown in FIGS. 2A and 2B.

First membrane residue stream 453, which is still at high pressure, flows as a feed stream, 460, across the feed surface of second membrane 452. The permeate side of the membrane is maintained at lower pressure to provide a driving force for transmembrane permeation. $C_1$ and $C_2$ hydrocarbons permeate the membrane preferentially, resulting in hydrocarbon-enriched permeate stream, 465, and hydrocarbon-depleted residue stream, 463. Typically, the feed side is maintained at a pressure within the range of about 20 bar g to about 40 bar g. The permeate side is typically maintained at a pressure within the range of about 1 bar g to about 25 bar g; preferably, the permeate side is maintained at a pressure of 7 bar g or less.

Hydrocarbon-depleted membrane residue stream 463 is withdrawn from the feed side of second membrane unit 461. Stream 463—the major component of which is now the combined contaminants hydrogen and carbon monoxide—can either be flared or sent for use as fuel gas.

Hydrocarbon-enriched permeate stream 465 is withdrawn from the permeate side of the second membrane unit 461. Second permeate stream 465 can then be routed back to the process at one (or both) of position E or position F, as discussed above with respect to the process embodiment shown in FIG. 3.

As yet another option, second permeate stream 465 can be routed back to any point in the MTP conversion operation where the pressure is no more than 7 bar g.

The invention is now further described by the following examples, which are intended to be illustrative of the invention, but are not intended to limit the scope or underlying principles in any way.

EXAMPLES

Example 1

Comparative Example—Conventional MTP Process
(not in Accordance with the Invention)

The calculations that follow were performed using a computer process simulation program (ChemCad 6.3.2, ChemStations, Houston, Tex.) which was modified with differential element subroutines for the membrane separation steps (as applicable).

The following calculation was performed according to the process schematic illustrated in FIG. 1A, for a conventional MTP process. The plant was assumed to be processing 4,400 tons of methanol per day, and producing 1,370 tons of propylene per day.

As shown in FIG. 1A, the portion of the lights stream from the de-ethanizer overhead that is to be purged to the fuel line is sent first to compression, 133, cooling, and phase separation, 147, to separate out some of the ethylene in stream 136. Stream 135 is sent as purge to the fuel line. Results of the calculation are presented in Table 1.

TABLE 1

Conventional MTP Process (not in accordance with the invention)

| Stream: | Flare/Fuel Gas (135) | Recycle Stream (136) |
|---|---|---|
| Mass Flow (kmol/h) | 79 | 390 |
| Mass Flow (kg/h) | 1,395 | 9,935 |
| Temp. (° C.) | −48 | −48 |
| Pressure (bar g) | 34 | 34 |
| Methane (mol %) | 39.8 | 17.9 |
| Ethylene (mol %) | 38.6 | 80.5 |
| Carbon Monoxide (mol %) | 0.16 | 0.03 |
| Hydrogen (mol %) | 21.5 | 1.5 |
| Methane (kg/h) | 503 | 1,121 |
| Ethylene (kg/h) | 854 | 8,800 |
| Carbon Monoxide (kg/h) | 3.5 | 3.1 |
| Hydrogen (kg/h) | 34.1 | 12.1 |

As can be seen from Table 1, the purge stream, 135, still contains about 854 kg/h ethylene. It would be therefore be helpful to have a process that recycles more of the ethylene back to the MTP process.

Example 2

Process of the Invention, with One Membrane Separation Step, and Recycle of $C_1$ and $C_2$ Hydrocarbons to the De-Ethanizer The following calculation was performed according to the process schematic illustrated in FIG. 2B, where a stream, 132, containing mostly inerts and $C_1$ and $C_2$ hydrocarbons is withdrawn from the top of the de-ethanizer column 127 and processed as feed stream 250 in membrane separation unit 251 containing membranes 252 that are selective to hydrogen over $C_1$ and $C_2$ hydrocarbons. Hydrocarbon-enriched membrane residue stream 253 is then combined with stream 132 and routed as combined stream 254 to the process upstream of compressor 133, from where it is passed as compressed stream 151 via condenser 147, and streams 136 and 141 to hydrocarbon recycle at position D.

The membrane 252 was assumed to have a hydrogen/ethylene selectivity of 14.3 and a hydrogen permeance of 672 gpu. Membrane area was assumed to be 76 m². Results of the calculation are presented in Table 2.

TABLE 2

Process of the Invention, with One Membrane Separation Step, and Recycle of $C_1$ and $C_2$ Hydrocarbons to the De-ethanizer

| Stream: | Membrane Feed (250) | Membrane Permeate/Fuel Gas (255) | Membrane Residue/ Recycle Stream (253) |
|---|---|---|---|
| Mass Flow (kmol/h) | 168 | 33.5 | 134 |
| Mass Flow (kg/h) | 3,080 | 364 | 2,716 |
| Temp. (° C.) | −10 | −10 | −10 |
| Pressure (bar g) | 34 | 1 | 34 |
| Methane (mol %) | 45.7 | 29.5 | 49.7 |
| Ethylene (mol %) | 38.0 | 17.7 | 43.1 |
| Carbon Monoxide (mol %) | 0.16 | 0.3 | 0.12 |
| Hydrogen (mol %) | 16.2 | 52.4 | 7.1 |
| Methane (kg/h) | 1,229 | 159 | 1,071 |
| Ethylene (kg/h) | 1,788 | 167 | 1,622 |
| Carbon Monoxide (kg/h) | 7.5 | 3.0 | 4.6 |
| Hydrogen (kg/h) | 54.7 | 35.4 | 19.3 |

As can be seen from Table 2, flare/fuel gas stream 255 contains 167 kg/h ethylene, as opposed to 854 kg/h ethylene for the conventional MTP process—a reduction of about 80%.

Example 3

Process of the Invention, with Two Membrane Separation Steps and Recycle of $C_1$ and $C_2$ Hydrocarbons to Either the Compressor Downstream of the Quench Column or to the MTP Reactor The following calculation was performed according to the process schematic illustrated in FIG. 4, where a stream 134 containing mostly inerts and $C_1$ and $C_2$ hydrocarbons is withdrawn from the top of the de-ethanizer column 127 and processed in a first membrane separation unit, 451, containing membranes, 452, that are selective to hydrogen over $C_1$ and $C_2$ hydrocarbons, followed by processing of the residue stream, 453, from the first membrane unit in a second membrane unit, 461, containing membranes, 462, that are selective to $C_1$ and $C_2$ hydrocarbons over hydrogen.

Hydrocarbon-enriched second membrane permeate stream 465 can then be recycled back to the process at one (or both) of two positions:

To position E: After quench column 106 and upstream of main compressor 108.
To position F: Directly back to MTP reactor 104.

First membrane 452 was assumed to have a hydrogen/ethylene selectivity of 14.3 and a hydrogen permeance of 672 gpu. First membrane area was assumed to be 55 m². Second membrane 462 was assumed to have an ethylene/hydrogen selectivity of 4.3 and a $C_2$ hydrocarbon permeance of 456 gpu. Second membrane area was assumed to be 48 m². Results of the calculation are presented in Table 3.

TABLE 3

Process of the Invention, with Two Membrane Separation Steps, and Recycle of $C_1$ and $C_2$ Hydrocarbons to Either the Compressor Downstream of the Quench Column, or to the MTP Reactor

| Stream: | First Membrane Feed (134) | First Membrane Permeate (455) | First Membrane Residue (453) | Second Membrane Residue/ Fuel Gas (463) | Second Membrane Permeate/ Recycle Stream (465) |
|---|---|---|---|---|---|
| Mass Flow (kmol/h) | 79 | 25.4 | 53.5 | 9.2 | 44.3 |
| Mass Flow (kg/h) | 1,395 | 367 | 1,129 | 143 | 986 |
| Temp. (° C.) | −48 | −10 | −10 | −52 | −31 |
| Pressure (bar g) | 34 | 1 | 34 | 34 | 2.1 |
| Methane (mol %) | 39.8 | 25.9 | 46.4 | 75.9 | 40.2 |
| Ethylene (mol %) | 38.6 | 18.4 | 48.2 | 10.7 | 55.9 |
| Carbon Monoxide (mol %) | 0.16 | 0.28 | 0.10 | 0.24 | 0.07 |
| Hydrogen (mol %) | 21.5 | 55.4 | 5.4 | 12.1 | 3.7 |
| Methane (kg/h) | 503 | 105 | 398 | 112 | 286 |
| Ethylene (kg/h) | 854 | 131 | 723 | 27.7 | 696 |
| Carbon Monoxide (kg/h) | 3.5 | 2.0 | 1.5 | 0.6 | 0.9 |

TABLE 3-continued

Process of the Invention, with Two Membrane Separation Steps, and Recycle of $C_1$ and $C_2$ Hydrocarbons to Either the Compressor Downstream of the Quench Column, or to the MTP Reactor

| Stream: | First Membrane Feed (134) | First Membrane Permeate (455) | First Membrane Residue (453) | Second Membrane Residue/ Fuel Gas (463) | Second Membrane Permeate/ Recycle Stream (465) |
|---|---|---|---|---|---|
| Hydrogen (kg/h) | 34.1 | 28.3 | 5.8 | 2.4 | 2.3 |

As can be seen from Table 3, together, first membrane permeate stream 455 and flare/fuel gas stream 463 contain a total of 158.7 kg/h ethylene, as opposed to 854 kg/h ethylene for the conventional MTP process—a reduction of about 81%.

I claim:

1. A methanol-to-propylene conversion process, comprising:
   (a) performing an operation to convert methanol to propylene, said operation including at least one reaction step and at least one propylene recovery step;
   (b) withdrawing from the operation a gas stream comprising hydrogen, carbon monoxide, and $C_1$ and $C_2$ hydrocarbons;
   (c) providing a membrane having a feed side and a permeate side, wherein the membrane is selective to hydrogen over $C_2$ hydrocarbons;
   (d) passing the gas stream as a feed stream across the feed side;
   (e) withdrawing from the permeate side a permeate stream that is depleted in $C_2$ hydrocarbons relative to the gas stream;
   (f) withdrawing from the feed side a residue stream that is enriched in $C_2$ hydrocarbons relative to the gas stream; and
   (g) passing the residue stream as a recycle stream back to step (a).

2. A process in accordance with claim 1, wherein the residue stream is recycled back to a point of the operation where the pressure is at least 1 bar less than the feed stream pressure.

3. A process in accordance with claim 1, wherein the residue stream is recycled back to a compressor located downstream of a de-ethanizer column.

4. A process in accordance with claim 1, wherein the residue stream is recycled back to a compressor downstream of a quench column.

5. A process in accordance with claim 1, wherein the residue stream is recycled back to a methanol-to-propylene reactor.

6. A process in accordance with claim 1, wherein the membrane comprises a glassy polymer.

7. A process in accordance with claim 1, wherein the membrane has a selectivity for hydrogen over ethylene of at least 10.

8. A process in accordance with claim 1, wherein the membrane has a hydrogen permeance of at least about 500 gpu.

9. A process in accordance with claim 1, wherein the membrane is also selective for carbon oxides over $C_1$ hydrocarbons.

10. A methanol-to-propylene conversion process, comprising:
    (a) performing an operation to convert methanol to propylene, said operation including at least one reaction step and at least one propylene recovery step;
    (b) withdrawing from the operation a gas stream comprising hydrogen, carbon monoxide, and C and $C_2$ hydrocarbons;
    (c) providing a first membrane having a first feed side and a first permeate side, wherein the first membrane is selective to hydrogen over $C_2$ hydrocarbons;
    (d) passing the gas stream across the first feed side;
    (e) withdrawing from the first permeate side a first permeate stream that is depleted in $C_2$ hydrocarbons relative to the gas stream;
    (f) withdrawing from the first feed side a first residue stream that is enriched in $C_2$ hydrocarbons relative to the gas stream;
    (g) providing a second membrane having a second feed side and a second permeate side, wherein the second membrane is selective to $C_2$ hydrocarbons over hydrogen;
    (h) passing the first residue stream across the second feed side;
    (i) withdrawing from the second feed side a second residue stream that is depleted in $C_2$ hydrocarbons relative to the first residue stream;
    (j) withdrawing from the second permeate side a second permeate stream that is enriched in $C_2$ hydrocarbons relative to the first residue stream; and
    (k) passing the second permeate stream as a recycle stream back to step (a).

11. A process in accordance with claim 10, wherein the second permeate stream recycled back to a point of the operation where the pressure is no more than 7 bar g.

12. A process in accordance with claim 10, wherein the second permeate stream is recycled back to a compressor downstream of a quench column.

13. A process in accordance with claim 10, wherein the second permeate stream is recycled back to a methanol-to-propylene reactor.

14. A process in accordance with claim 10, wherein the first membrane comprises a glassy polymer.

15. A process in accordance with claim 10, wherein the first membrane has a selectivity for hydrogen over ethylene of at least 10.

16. A process in accordance with claim 10, wherein the first membrane has a hydrogen permeance of at least about 500 gpu.

17. A process in accordance with claim 10, wherein the second membrane comprises a rubbery polymer.

18. A process in accordance with claim 10, wherein the second membrane has a selectivity for ethylene over hydrogen of at least 4.

19. A process in accordance with claim 10, wherein the second membrane has a $C_2$ hydrocarbon permeance of at least about 400 gpu.

20. A process in accordance with claim 10, wherein the first membrane is also selective for carbon oxides over $C_2$ hydrocarbons.

21. A process in accordance with claim 10, wherein the second membrane is also selective for $C_2$ hydrocarbons over carbon oxides.

* * * * *